(12) United States Patent
Oberstadt

(10) Patent No.: US 6,717,028 B1
(45) Date of Patent: Apr. 6, 2004

(54) BOND PATTERN

(75) Inventor: Gregory Allen Oberstadt, New London, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 120 days.

(21) Appl. No.: 09/689,364

(22) Filed: Oct. 12, 2000

Related U.S. Application Data

(60) Provisional application No. 60/229,190, filed on Aug. 30, 2000.

(51) Int. Cl.[7] ................................. A61F 13/15
(52) U.S. Cl. ................. 604/365; 604/366; 604/385.01; 604/385.23; 428/198; 156/291
(58) Field of Search .................. 264/210.1, 211.14, 264/216, 309, 355, 168; 427/207.1, 208.2, 208.4, 208.6, 284, 285; D15/126; D5/61, 52, 53, 5; 604/365, 385.01, 385.23; 442/59, 149, 374; 156/60, 61, 291; 428/198

(56) References Cited

U.S. PATENT DOCUMENTS

| | | | |
|---|---|---|---|
| 3,720,554 A | * 3/1973 | Stumpf | 156/62.6 |
| 4,493,868 A | 1/1985 | Meitner | 428/171 |
| 4,699,823 A | * 10/1987 | Kellenberger et al. | 428/129 |
| 4,781,966 A | 11/1988 | Taylor | 428/152 |
| 5,124,111 A | * 6/1992 | Keller et al. | 264/555 |
| 5,342,647 A | * 8/1994 | Heindel et al. | 427/2.31 |
| 5,451,219 A | 9/1995 | Suzuki et al. | 604/385.2 |
| 5,540,976 A | * 7/1996 | Shawver et al. | 428/198 |
| 5,591,155 A | * 1/1997 | Nishikawa et al. | 604/393 |
| 5,681,645 A | * 10/1997 | Strack et al. | 428/196 |
| D390,708 S | * 2/1998 | Brown | D5/61 |
| D412,508 S | * 8/1999 | Witsken | |
| 5,932,284 A | * 8/1999 | Reynolds | 427/207.1 |
| 5,964,742 A | * 10/1999 | McCormack et al. | 604/380 |
| 6,036,805 A | * 3/2000 | McNichols | 156/227 |
| 6,123,792 A | * 9/2000 | Samida et al. | 156/73.1 |

FOREIGN PATENT DOCUMENTS

| | | | | |
|---|---|---|---|---|
| EP | 0 657 153 A2 | 6/1995 | | A61F/13/15 |
| EP | 0 657 153 B1 | 6/1995 | | A61F/13/15 |
| WO | WO 99/14039 | 3/1999 | | B32B/5/26 |

\* cited by examiner

*Primary Examiner*—Weilun Lo
*Assistant Examiner*—Jacqueline F Stephens

(57) ABSTRACT

Bonded composites, and absorbent articles made with such bonded composites. The bonded composites have first and second thin-section elements bonded to each other by bonds defining a bond pattern.

79 Claims, 7 Drawing Sheets

BOND PATTERN

CROSS-REFERENCE TO RELATED APPLICATIONS

This application claims priority to Provisional Application Ser. No. 60/229,190 filed Aug. 30, 2000.

BACKGROUND

The present invention relates to a bonded composite of a first thin-section element of sheet material and a second thin-section element. bonded together by bond elements defining a bond pattern. More particularly, one of the contemplated applications for the present invention is in bonding e.g. an outer cover and a body-side liner thin-section elements of absorbent articles to one another, as a bonded composite.

Absorbent articles are known as personal care hygiene products. Such absorbent articles find use, for example, as diapers, training pants, incontinence inlays, and women's sanitary pads. Such absorbent articles can absorb and store liquid bodily excretions such as urine, menstrual fluid, or blood. Women's sanitary pads are used, for example, to absorb the liquids excreted prior to, during and after menstruation.

In absorbent articles, the portions of the article where different layers or components are bonded to each other tend to incur significant stress concentrations, and in absorbent articles using conventional bond patterns, tend to fracture at such bonded locations under such stresses. In conventional patterns used in absorbent articles, bond locations are disposed in uniform and crossing straight lines and straight rows of circular bond elements. The inventors herein have noted that, when the absorbent article tears, the tear tends to propagate along the side edge of the bond pattern. Tearing properties of such conventional bond patterns can be compared to tearing of a paper form along a perforated line of weakness.

The problem for the present invention is thus to provide a bonded composite employing a bond pattern and an absorbent article implementing the bond pattern, whereby the position of adjacent bond locations is not linear, and whereby, the configuration of the bond pattern discourages fracture of the bonded composite or absorbent article.

It is an object of this invention to reduce the tendency of the bonded composite or absorbent article to tear, by employing bonding locations and configurations that prevent straight-line fracture and thereby spread a stressing force throughout the bonding pattern.

It is another object to configure the bonding locations such that a stressing force, when imposed on a respective bond element, is distributed into the interior portion of the bond pattern, forcing a potential fracture to propagate in a longer, and more-difficultly-propagated, non-straight path.

SUMMARY

In a first family of embodiments, the invention comprises a bonded composite. The bonded composite has, as a first thin-section element, a first layer of thin-section sheet material, and a second thin-section element bonded to the first thin-section element by bonds defining a tear-resistant bond pattern. The tear-resistant bond pattern has a length, and a width represented by first and second side edges of the bond pattern. The bond pattern reflects application of pressure urging the first and second thin-section elements toward each other in face-to-face relationship to form an array of separate, distinct, and spaced interlocking arcuate bond elements affixing the first and second thin-section elements to each other in the process of fabricating the absorbent article. Each bond element has spaced first and second ends and corresponding end portions, and an arcuate intermediate portion between the first and second end portions. At least portions of the arcuate intermediate portions of selected ones of the bond elements are disposed toward respective side edges of the bond pattern. The ends of the respective bond elements are disposed inwardly of the side edges.

Substantial portions of the arcuate intermediate portions of selected ones of the bond elements are disposed toward respective side edges of the bond pattern.

The shape of the intermediate portion of a respective bond element can comprise a substantial portion of an ellipse, a substantial portion of a circle, or a substantial portion of an hyperbola.

The first end portion of a first bond element can intersect or cross a first imaginary line connecting the first and second ends of a second bond element, and the second end portion of the second bond element can intersect or cross a second imaginary line connecting the first and second ends of the first bond element.

The intermediate portions of respective ones of the bond elements can include inflections, and can extend from the first side of the bond pattern to the second side of the bond pattern.

The bond pattern may comprise an array of the bond elements arranged in a longitudinally-repeating pattern, such that respective ones of the bond elements are positioned at repeated width locations and at repeated longitudinal spacings along the length of the bond pattern.

The width of the bond pattern between the first and second side edges can be about 4 millimeters to about 14 millimeters, preferably about 5 millimeters to about 12 millimeters.

The arcuate bond elements can be activated by application of thermal energy, ultrasonic-frequency energy, and/or adhesives, to at least one of the first and second thin-section elements.

At least one of the first thin-section element and the second thin-section element can comprise a polymeric material selected from the group consisting of polyolefins, polyesters, and polyamides, and copolymers, mixtures, and blends of such polymeric materials.

At least one of the first thin-section element and the second thin-section element can comprise a fibrous web defining a multiplicity of randomly-spaced small openings extending from a major surface of the web into the interior of the web.

In a second family of embodiments, the invention comprises an absorbent article having a front portion and a rear portion, and a crotch portion between the front portion and the rear portion. The absorbent article comprises, as a first thin-section element, a first layer of thin-section sheet material, a second thin-section element bonded to the first thin-section element and correspondingly attached as an element of the absorbent article by bonds defining a tear-resistant bond pattern, and an absorbent core disposed adjacent one of the first thin-section element and the second thin-section element. The tear-resistant bond pattern has a length, and a width represented by first and second side edges of the bond pattern. The bond pattern reflects application of pressure urging the first and second thin-section elements toward each other in face-to-face relationship to form an array of separate, distinct, and spaced interlocking arcuate bond elements affixing the first and second thin-section elements to each other, in the process of fabricating the absorbent article. The bond elements have spaced first and second ends and corresponding end portions, and arcuate intermediate portions between the first and second end portions. At least portions of the arcuate intermediate portions of selected ones of the bond elements are disposed toward respective side edges of the bond pattern, and the ends of the respective bond elements are disposed inwardly of the side edges.

In some embodiments, the first thin-section element comprises an outer cover, and the second thin-section element comprises a body side liner, and at least one of the outer cover and the body side liner comprises a polymeric material selected from the group consisting of polyolefins, polyesters, and polyamides, and mixtures, copolymers, and blends of such polymeric materials.

In some embodiments, the first thin-section element comprises an outer cover and the outer cover comprises a polymeric film having a composition comprising primarily polyethylene or polypropylene, or a mixture or copolymer comprising polyethylene and polypropylene.

In some embodiments, the second thin-section element comprises a body side liner and the body side liner comprises a material selected from the group comprising porous foams, reticulated foams, apertured polymeric films, polymeric fibers, and natural fibers. The body side liner can comprise a mixture of materials selected from the group consisting of porous foams, reticulated foams, apertured polymeric films, polymeric fibers, and natural fibers.

In preferred embodiments, the absorbent core comprises a matrix of hydrophilic fibers.

In some embodiments of the absorbent article, the length of the bond pattern extends from the front portion of the absorbent article to the rear portion of the absorbent article.

In other embodiments of the absorbent article, the crotch portion of the absorbent article is devoid of the bond pattern.

The absorbent article in the present invention can serve a variety of functions including but not limited to feminine hygiene articles, training pants, diapers, or adult incontinence products.

Figure 1A:
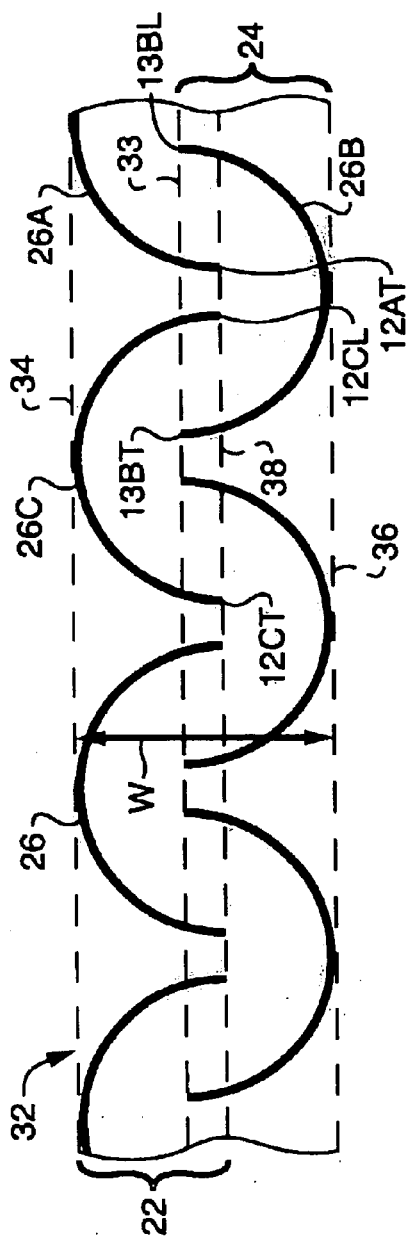
FIG. 1A shows a plan view of a representative first bond pattern of this invention.

The invention is not limited in its application to the details of construction or the arrangement of the components set forth in the following description or illustrated in the drawings. The invention is capable of other embodiments or of being practiced or carried out in other various ways. Also, it is to be understood that the terminology and phraseology employed herein is for purpose of description and illustration and should not be regarded as limiting. Like reference numerals are used to indicate like components.

DESCRIPTION OF THE ILLUSTRATED EMBODIMENTS

FIG. 1A shows a bond pattern 32 having a first side edge generally defined at 34 and a second side edge generally defined at 36. Bond pattern 32 has a first pattern combination 22 and a second opposing pattern combination 24, wherein portions of patterns 22 and 24 can overlap each other. Bond pattern 32 has a pattern length defined in terms of distance measured along either the first or second side edge, and a bond pattern width "W" represented by the distance between first side edge 34 and second side edge 36 of bond pattern 32. Correspondingly, the overall area of bond pattern 32 can be defined as the area which participates in absorbing and dissipating, by operation of the bond pattern, stresses received into the bond pattern from external sources.

Side edges 34, 36 can be specifically defined as outer extremities of those areas of the first and second thin-section elements which functionally participate with each other in absorbing and dissipating, by operation of the bond pattern, stresses received into the bond pattern.

Imaginary line 38 connects the ends of bond elements 26 on the portion of bond pattern 32 which is located between imaginary line 38 and first side edge 34. Such bond elements make up pattern combination 22. Correspondingly, imaginary line 33 connects the ends of bond elements 26 on the portion of bond pattern 32 which is located between imaginary line 33 and second side edge 36. Such bond elements make up pattern combination 24. Pattern combinations 22 and 24 can be substantially the same and are illustrated as being employed as off-set mirror images of each other, although the first and second opposing pattern combinations can be positioned along the length of the pattern such that the opposing pattern combinations are asymmetric with respect to each other. While the opposing patterns may be asymmetric with respect to each other, both pattern combination 22 and opposing pattern combination 24 are preferably internally symmetric. as well as being symmetric with respect to the length of bond pattern 32.

Bond pattern 32 is defined by a combination of bond elements 26. A plurality of bond elements which establishes repeated element combinations defines a bond segment, although not all bond elements 26 need be defined in bond segments. Therefore, a similar bond pattern using an orphan bond element which does not repeat regularly, or which is so far outside the rest of the bond pattern that such orphan element does not participate in absorbing and dissipating, by operation of the bond pattern, stresses received into the bond pattern, will still be anticipated by the present invention.

Bond pattern 32 comprises an array of separate. distinct, and spaced bond elements 26. Bond pattern 32 can comprise repeating bond segments, each repeating bond segment comprising a bond element configuration consistent from bond segment to bond segment.

Figure 1B:
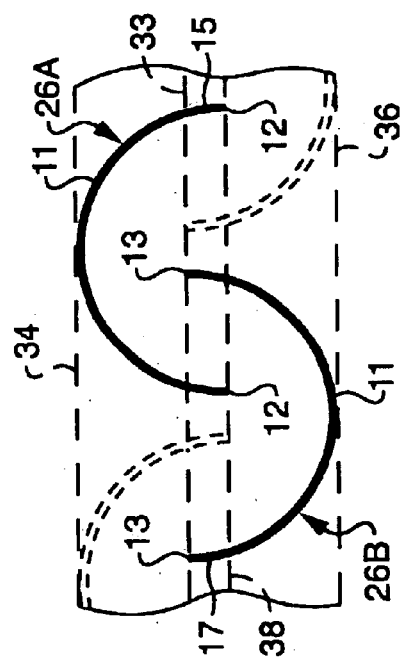
FIG. 1B is an enlarged view of a portion of the bond pattern of FIG. 1A.

Referring to FIG. 1B, substantial portions of arcuate intermediate portions 11 of the bond elements 26 are disposed toward respective side edges 34, 36 of bond pattern 32. The shape of intermediate portion 11 of a respective bond element 26 can comprise, without limitation, a substantial portion of an ellipse, a substantial portion of a circle, or a substantial portion of an hyperbola. A "substantial portion" of a circle or an ellipse or an hyperbola can be more or less than half of a 360 degree radial expression of the arc. Additionally, the arcuate intermediate portion need not have a constant radius nor be symmetric.

As illustrated in FIG. 1B, ends 12 of a first bond element 26A can intersect or cross first imaginary line 33 which connects first and second ends 13 of second bond element 26B, and ends 13 of second bond element 26B can intersect or cross second imaginary line 38 which connects first and second ends 12 of first bond element 26A. End portions 15, 17 of the respective bond elements are associated with and contain the ends of the respective bond elements. While the ends of the bond elements are contained within the end portions of the respective elements, the end portions can be arcuate.

Figure 1C:
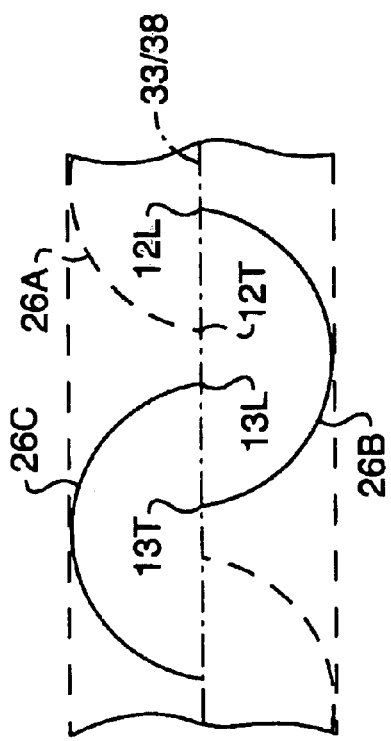
FIG. 1C shows a modification of FIG. 1A wherein ends of the bond elements intersect imaginary lines connecting ends of adjacent bond elements.
Figure 1D:
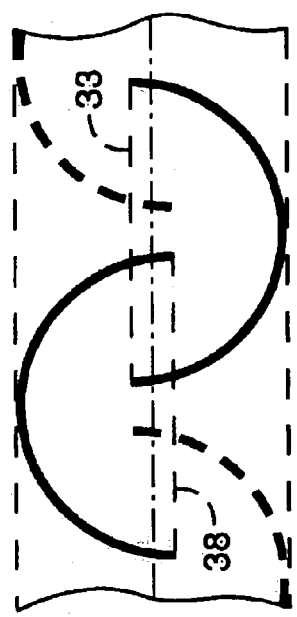
FIG. 1D further illustrates the bond pattern of FIG. 1A wherein ends of the bond elements cross imaginary lines connecting ends of adjacent bond elements.

FIG. 1C shows an intersecting bond relationship wherein the first and second imaginary lines are superimposed one on the other. Other embodiments employ separate and distinct first and second imaginary lines as in FIG. 1D.

Figure 7:
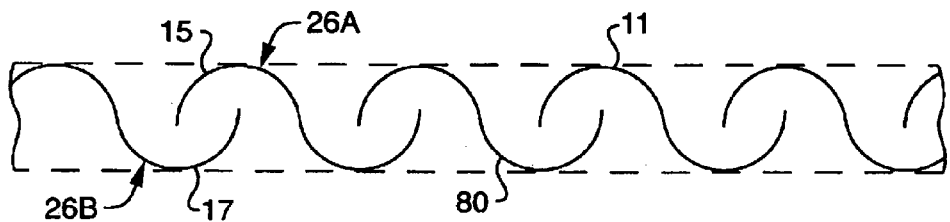
FIG. 7 shows a plan view of a second bond pattern illustrative of the invention.
Figure 8:
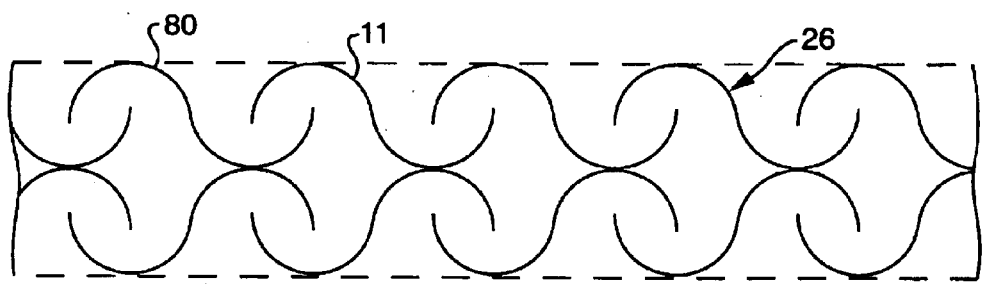
FIG. 8 shows a plan view of a third bond pattern illustrative of the invention.

Intermediate portions 11 of respective ones of bond elements 26 can include inflections 80, namely changes in curvature between concave and convex, shown in FIGS. 7 and 8, and can extend from the first side of the bond pattern to the second side of the bond pattern. In bond elements 26 which include inflections 80, first end portion 15 of a first bond element 26A can intersect or cross a first imaginary line connecting the first and second ends of a second bond element, and second end portion 17 of second bond element 26B can intersect a second imaginary line connecting the first and second ends of the first bond element.

The bond pattern may comprise an array of bond elements 26 arranged in a longitudinally-repeating pattern, such that respective ones of the bond elements are positioned at repeated width locations and at repeated longitudinal spacings along the length of the bond pattern. The width of the bond pattern between the first and second side edges can be about 4 millimeters to about 14 millimeters, preferably about 5 millimeters to about 12 millimeters, more preferably about 6 millimeters to about 10 millimeters, even more preferably about 7 millimeters to about 9 millimeters. Narrower patterns can employ less material. Wider patterns have greater potential for effectively absorbing and dissipating stresses imposed on the pattern.

In preferred embodiments of the present invention, bond pattern 32 can be used to unite sheets of material along the entirety of the length of the material, or in the case of the examples cited, along the entirety of the length or width of an absorbent article.

In the alternative, bond pattern 32 can be used to intermittently unite segments spaced intermittently along the length of a thin section element.

Bond pattern 32 can be used to unite segments in a pattern having a bond pattern width varying along the length of the bond pattern.

Bond pattern 32 can be used to unite materials along a continuous defined length. In all of the previously mentioned embodiments, bond pattern 32 can be used to bond a relatively smaller element to a relatively larger element. Examples for use of the bond pattern in an absorbent article include, but are not limited to, bonding an ear to the outer cover, bonding a leg flap to the outer cover and/or body-side liner, and bonding containment flaps to the body-side liner.

Bond pattern 32 reflects application of pressure urging first and second elements toward each other in face-to-face relationship to form an array of separate, distinct, and spaced, optionally interlocking, arcuate bond elements 26 affixing the first and second elements to each other.

FIGS. 1A, 1B, 1C, 1D, 2, 4, 7, and 8 illustrate such interlocking. Referring to, for example, FIG. 1A, considering the right end of the bond pattern as being disposed toward a leading end of the bond pattern; considering the left end of the bond pattern as being disposed toward a trailing end of the bond pattern; each pattern element 26 can be, in general, considered as being a leading pattern element with respect to the pattern element next disposed toward the trailing end of the bond pattern.

Correspondingly, each pattern element 26 can, in general, be considered as being a trailing pattern element with respect to the pattern element next disposed toward the leading end of the bond pattern. The first pattern element on the leading end, of course, has only a trailing pattern element; and the last pattern element on the trailing end, has only a leading pattern element.

In general, then, each pattern element is disposed between a leading pattern element, next toward the leading end of the bond pattern, and a trailing pattern element, next toward the trailing end of the bond pattern. Similarly, each pattern element has a leading end (e.g., 12L or 13L) and a trailing end, (e.g., 12T or 13T). For example, and referring to FIG. 1A, pattern element 26A has a first leading end (which would be nwnbered 12AL but is not shown) and a first trailing end 12AT. The next succeeding bond element, namely pattern element 26B, has a second leading end 13BL and a second trailing end 13BT. The subsequent succeeding bond element, namely pattern element 26C, has a third leading end 12CL and a third trailing end 12CT.

In the above numbering of the ends, the first two characters, 12 or 13, indicate the pattern portion with which the particular pattern element is associated. The third character, e.g., "A", "B", or "C", indicates the particular pattern element being addressed. The fourth character, e.g., "L" or "T", indicates whether a leading end or a trailing end is being addressed.

In all the above nomenclature, the words "leading" and "trailing" are relative terms which merely relate a particular pattern clement or an end of a pattern element, to an adjacent one of the pattern elements.

The figures, e.g., FIGS. 1A, 1B, 1C, 1D, 2, 4, 7, and 8, all illustrate the feature of the invention whereby the pattern elements 26 interlock by the trailing end of a relatively leading pattern element 26 trailing the leading end of the next succeeding pattern element. For example, and referring to e.g., FIGS. 1A and 1C, trailing end 12AT of pattern element 26A (leading pattern element relative to pattern element 26B) trails leading end 13BL of the next succeeding pattern element 26B (trailing pattern clement relative to pattern element 26A). Similarly, trailing end 13BT of pattern element 26B (leading pattern element relative to pattern clement 26C) trails leading end 12CL of the next succeeding pattern element 26C (trailing pattern element relative to pattern element 26B).

Because bond elements 26 extend into the interior of the bond pattern along both length directions, elements 26 can transfer to the interior of the bond pattern vectors of stresses coming from either length direction. Such transfer of stress into the interior of the bond pattern reduces the effective level of stress at the edge of the bond pattern. Thus, the arcuate portions of bond elements 26 tend to promote transfer of stresses to the interior of the bond pattern, and are effective to transfer stresses imposed on the bond pattern from any direction, away from the side edges and into the interior of the bond pattern. By distributing stresses to the interior of the bond pattern, the invention relieves a portion of the stress which is typically borne by side edge portions of the bond pattern, whereby the effective level of stress at a side edge, and resulting from an imposed force, is less than the stress which results from imposition of a corresponding force on a similar article bearing a conventional bond pattern. Thus, bond patterns of the invention can tolerate greater levels of overall stress than corresponding conventional bond patterns. Thus, not only do bond patterns of the invention reduce the tendency of conventional linearly-arranged bond patterns to tear along the side edges, such bond patterns are capable of tolerating and distributing greater amounts of stress than corresponding conventional bond patterns.

Figure 2:
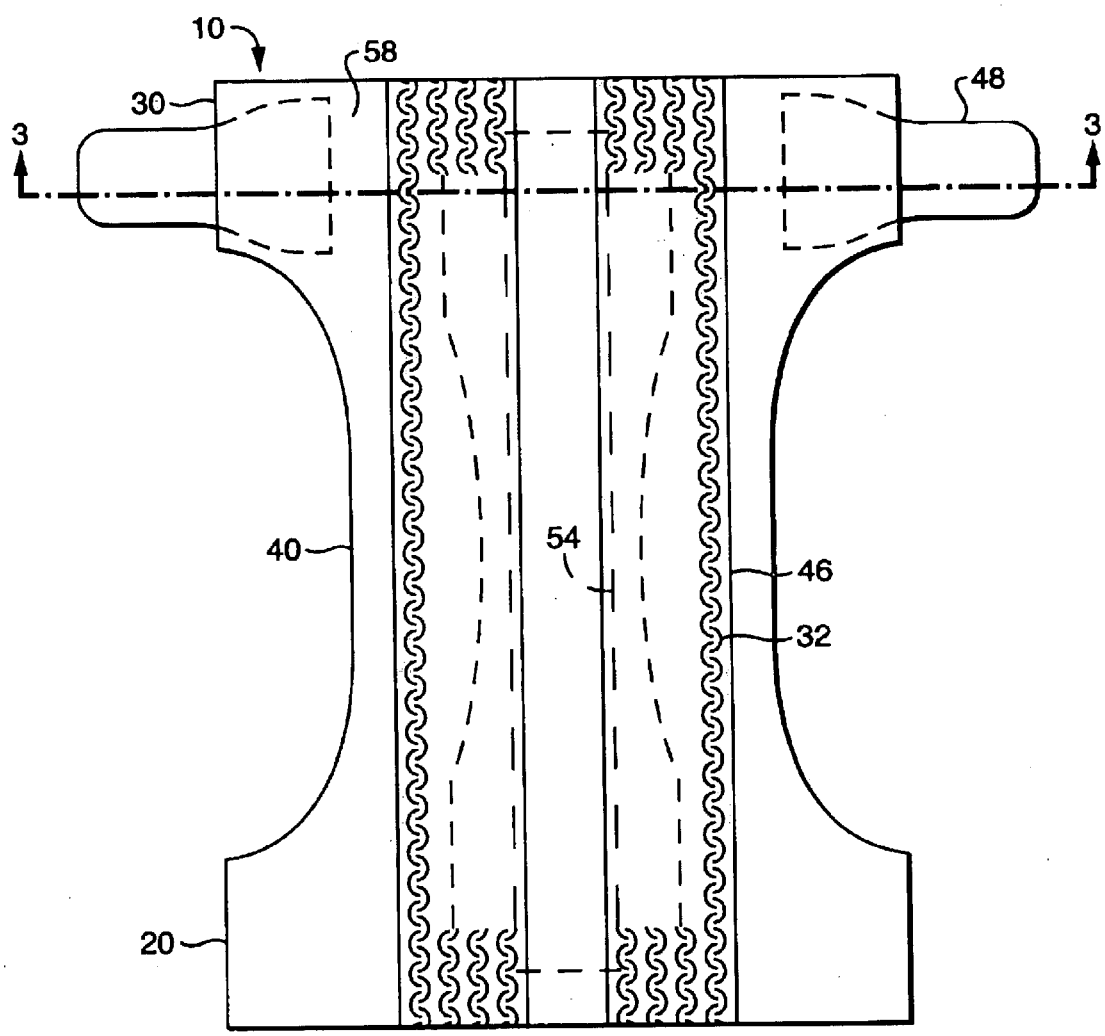
FIG. 2 shows a plan view of a stretched-out absorbent article using a bond pattern of the invention along the full length of the absorbent article.
Figure 3:
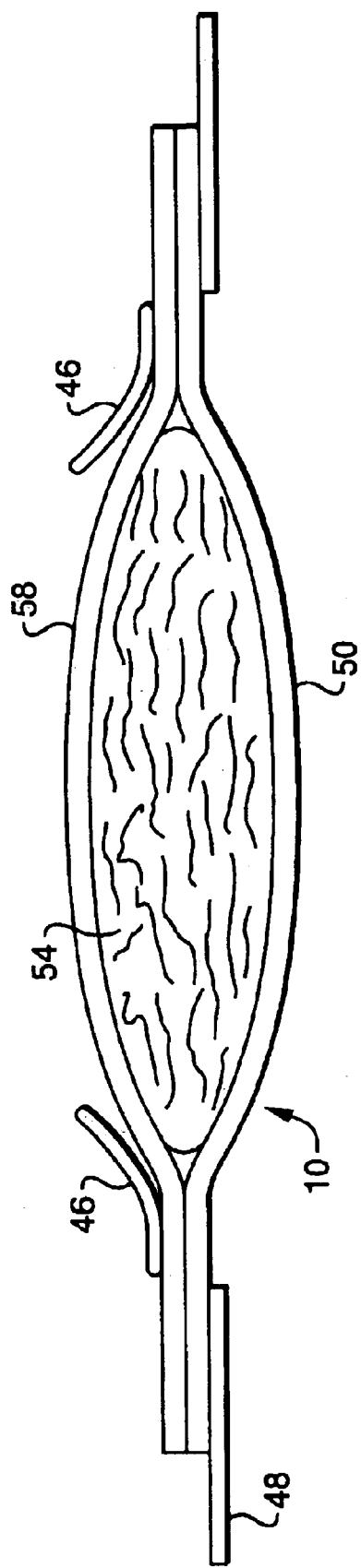
FIG. 3 shows a cross-sectional view of the absorbent article of FIG. 1 in a relaxed state.

An absorbent article 10, as shown in FIGS. 2–5, includes a front portion 20, a rear portion 30, and a crotch portion 40 which extends between front portion 20 and rear portion 30. Absorbent article 10 includes, as a first thin-section element, liquid impermeable outer cover 50, as a second thin-section element, liquid-permeable body-side liner 58, and a liquid-absorbent core 54 between the outer cover and the body side liner. Referring to FIG. 3. containment flaps 46 extend from body side liner 58, and diaper ears 48 are shown attached to outer cover 50.

Various woven and nonwoven fabrics can be used for body-side liner 58. For example, body-side liner 58 can be e.g. a meltblown or spunbonded or other non-woven web of polymeric material selected from the group consisting of polyolefins including polyethylenes and polypropylenes, polyesters, and polyamides, and mixtures, copolymers, and blends of such polymeric fibers. Body-side liner 58 may also comprise a carded and/or bonded web composed of natural and/or synthetic fibers. The body-side liner can be composed of a substantially hydrophobic material wherein the hydrophobic material is treated with a surfactant or otherwise processed to impart a desired level of wetability and hydrophilicity.

Body-side liner 58 can comprise nonwoven, spunbonded, polypropylene fabric fabricated with 2.8–3.2 denier fibers, formed into a web having a basis weight of about 22 grams per square meter and a density of about 0.06 grams per cubic centimeter. The fabric is then surface treated with about 0.3 weight percent of a surfactant. Body-side liner 58 typically comprises a fibrous web defining a multiplicity of small e.g. microporous openings randomly spaced between the fibers and according to location and orientation of the fibers, and extending from a major surface of the web into the interior of the web. Such small openings typically extend through the entirety of the thickness of the web.

Addressing structure, body-side liner 58 can be fabricated using material selected from the group consisting of porous foams, reticulated foams, apertured polymeric films, polymeric fibers, and natural fibers. Body-side liner 58 can comprise a multiplicity of components or layers which correspond to any of the materials disclosed herein. as well as others known in the art.

It is generally preferred that outer cover 50 of the absorbent article be formed from a material which is substantially impermeable to liquids. A typical outer cover 50 can be manufactured from a thin plastic film or other flexible liquid-impermeable material. For example, outer cover 50 can be formed from a film of polymeric material selected from the group consisting of polyolefins including polyethylenes and polypropylenes, polyesters, and polyamides, and mixtures, copolymers, and blends of such polymeric materials, having thicknesses, for example, of from about 0.012millimeter to about 0.13 millimeter.

In embodiments where outer cover 50 should have a more cloth-like feel, the outer cover can comprise a polyethylene film having a nonwoven web, such as a spunbonded web of polyolefin fibers, bonded to a surface thereof. For example, a polyethylene film having a thickness of about 0.015 millimeter can have thermally or otherwise bonded thereto a spunbonded web of polyolefin fibers having fiber thicknesses of from about 1.5 to about 2.5 denier per filament, which nonwoven web has a basis weight of e.g. about 24 grams per square meter.

Further, outer cover 50 can be formed of a woven or nonwoven fibrous web which has been totally or partially constructed or treated to impart a desired level of liquid impermeability to selected regions which are adjacent or proximate absorbent core 54.

Still further, outer cover 50 can optionally be composed of a micro-porous material which permits vapors to escape from absorbent core 54 and through outer cover 50 while preventing liquid exudates from passing through the outer cover.

One or both of outer cover 50 and body-side liner 58 can comprise a fibrous web defining a multiplicity of randomly-spaced small openings extending from a major surface of the web into the interior of the web. It is important to note that polymeric material such as the recited polyolefins including polyethylenes and polypropylenes, polyesters, and polyamides, and mixtures, copolymers, and blends of such polymeric materials can be used in either film form or in non-woven fiber form, for one or both of body-side liner 58 and outer cover 50. As to bodyside liner 58, films are apertured films. As to outer cover 50, fibrous webs are impermeable to e.g. aqueous liquid.

Included in the definition of polymeric material above are all routine, common, normal additives known to those skilled in the art of polymeric materials such as processing aids, chemical stabilizers, compatibilizers where more than one polymer is used, fillers, and the like.

Absorbent core 54 suitably comprises hydrophilic fibers, such as a web or matt or loose collection of cellulosic fluff, in combination with a high-absorbency material commonly known as superabsorbent material . Absorbent core 54 preferably comprises a mixture of superabsorbent hydrogel-forming particles and wood pulp fluff. In place of the wood pulp fluff, one can use synthetic, polymeric, meltblown fibers or a combination of meltblown fibers and natural fibers. The superabsorbent material can be substantially homogeneously mixed with the hydrophilic fibers or can be otherwise combined into absorbent core 54.

Alternatively, absorbent core 54 can comprise a laminate of fibrous webs and superabsorbent material or other suitable means of maintaining a superabsorbent material in a localized area. Absorbent core 54 can additionally comprise an uncreped through air dried paper web material known as UCTAD.

Absorbent core 54 can have any of a number of shapes. For example, absorbent core 54 can be rectangular, I-shaped or T-shaped. Absorbent core 54 is preferably narrower in the crotch portion than in the rear portion or the front portion, especially where the crotch portion of the absorbent article is narrower than the rear portion or the front portion.

The high-absorbency material in absorbent core 54 can be selected from natural, synthetic and modified natural polymers and materials. The high absorbency materials can be inorganic materials, such as silica gels, or organic compounds, such as cross-linked polymers. The high absorbency materials refer to any structure or composition, along with associated process, which renders normally water-soluble materials substantially water insoluble but swellable, whereby absorbent properties are available but the swelled material is substantially immobile after absorbing water-based liquids. Such superabsorbent material can be fabricated by creating e.g. physical entanglement, crystalline domains. covalent bonds, ionic complexes and associations, hydrophilic associations such as hydrogen bonding, and hydrophobic associations or Van der Waals forces.

The absorbent article in the present invention can serve a variety of functions including, but not limited to, a feminine hygiene article, diaper, training pants, disposable swim wear, disposable adult underwear, or adult incontinence product.

Figure 6:
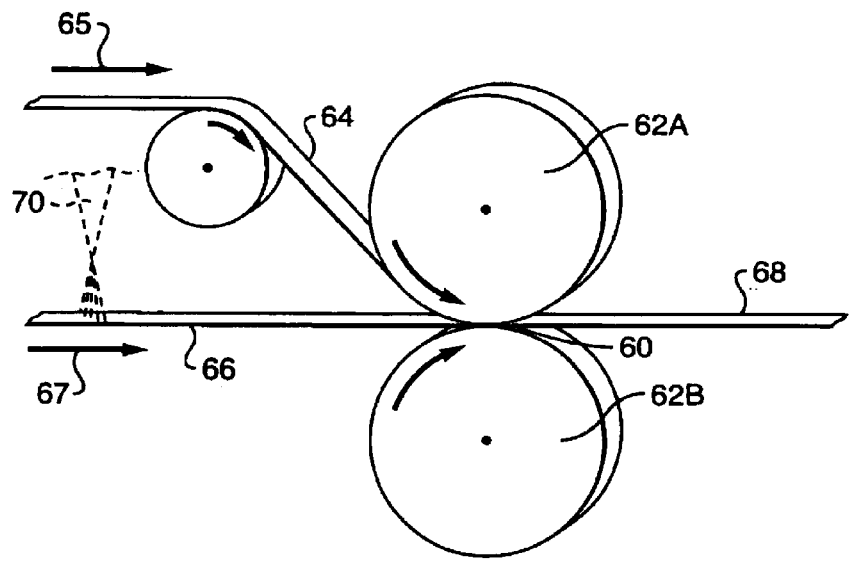
FIG. 6 shows a representative side pictorial view of a bonding nip such as can be used in continuous bonding processes employing bond patterns of the invention.

FIG. 6 represents a side pictorial view of a bonding nip 60 such as can be used in continuous bonding processes employing bond patterns of the invention. Bonding nip 60 is formed between two rotating rolls 62A. 62B. Rolls 62A, 62B can be mounted at any angle with respect to each other, so long as energy can be transmitted between the rolls to promote bonding. In FIG. 6, rolls 62A, 62B are mounted in a vertical orientation, such that roll 62A is located vertically over roll 62B. To create the bond pattern of the invention, web 64 and web 66 are fed from the left side of FIG. 6 as indicated by respective arrows 65, 67, and are urged toward each other in face-to-face relationship, in bonding nip 60, to form an array of separate, distinct, and spaced elongate bond elements affixing the first and second thin-section sheet materials to each other according to the bond pattern illustrated in e.g. FIG. 1A. The bond pattern, as well as the individual bond elements, can be activated by a variety of methods including but not limited to applying pressure, thermal energy e.g. in combination with pressure and/or ultrasonic-frequency energy in combination with pressure, to the webs at bonding nip 60.

The workpiece being defined for this illustration can include one or more of web 64, web 66, and the resultant bonded composite 68 of webs 64 and 66.

As an alternative to thermal energy or ultrasonic energy, e.g. chemical adhesives e.g. in combination with pressure at nip 60 can be used to create the bond pattern. FIG. 6 indicates an optional use of adhesive in combination with pressure at nip 60 instead of adhesion via pressure alone, thermal energy alone, or ultrasonic energy alone. While optional adhesive applicator 70 shows the adhesive being applied as a spray to web 66, optional adhesive applicator 70 is meant to be representative of various other known methods of positioning adhesive between web 64 and web 66. Such other methods include but are not limited to coating from a coating roll, dip applications, wire rod spreaders, and the like. As with the methods of obtaining adhesion, the types of chemical adhesive contemplated for this invention run the full range of all known adhesives which are suitable for bonding the materials of interest, for example and without limitation, contact adhesives, pressure sensitive adhesives, hot melt adhesives, and two-part chemically activated adhesives.

Figure 4:
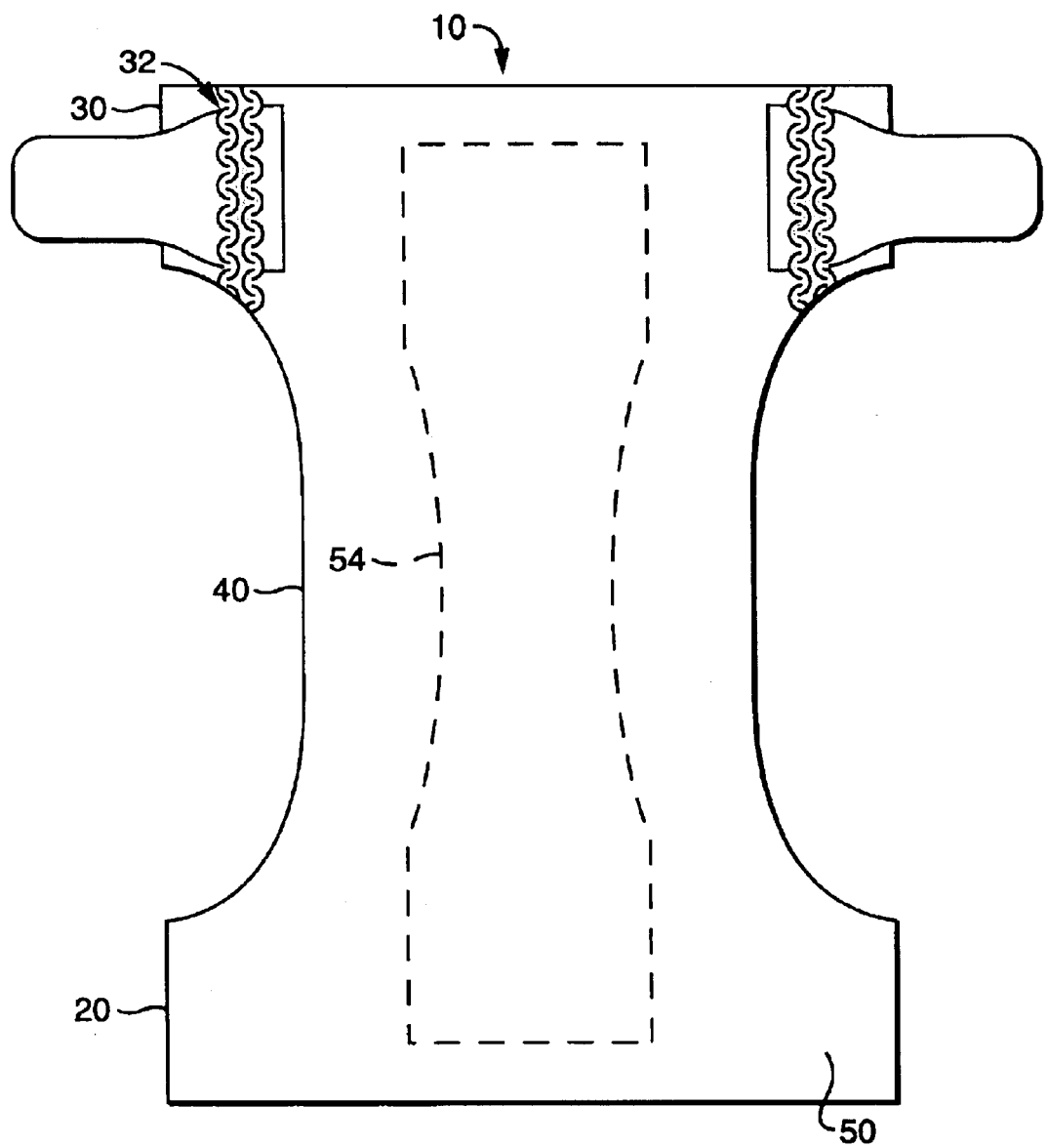
FIG. 4 shows a plan view of a stretched-out absorbent article as in FIG. 2 but using a bond pattern which is confined to the rear portion of the absorbent article, and which is used to bond ears to the absorbent article substrate.
Figure 5:
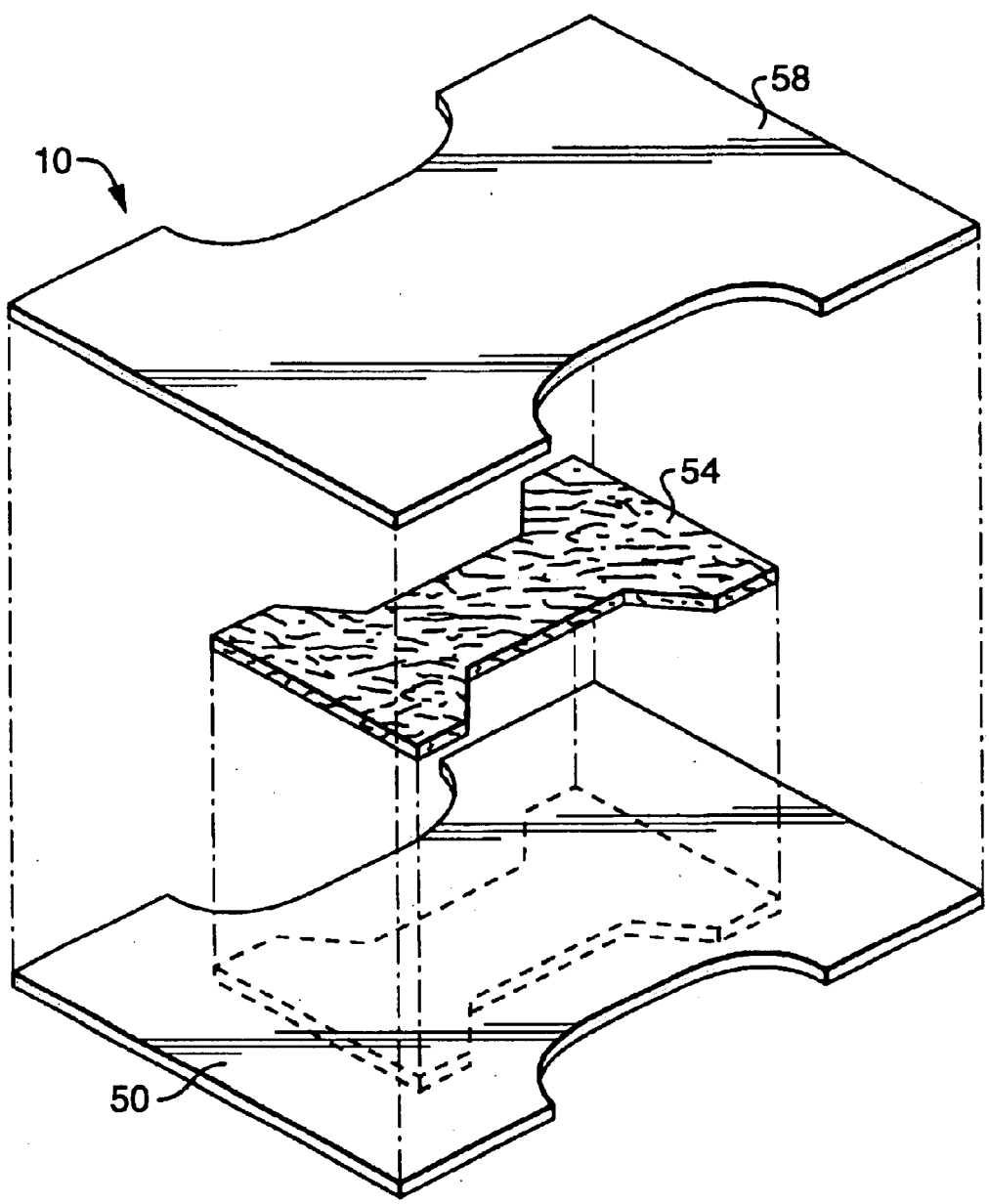
FIG. 5 shows an exploded pictorial view of an absorbent article as in FIG. 2.

In the absorbent article embodiments illustrated in the FIGURES, the illustrated bond patterns created by the process represented in FIG. 6 can represent an overall bond pattern outside absorbent core 54, or can e.g. join containment flaps 46 to body side liner 58 at locations illustrated in FIG. 2, or can join ears 48 to outer cover 50 as illustrated in FIG. 4. As stated previously, such articles typically comprise an assemblage of two or more layers or partial layers, along with other elements. Composition of materials of the respective layers can be the same, or different. Typical such web materials are woven or non-woven fabrics, or polymer film.

The bond pattern, as well as the individual bond elements, can be activated by a variety of methods including but not limited to applying pressure, thermal energy and pressure, or ultrasonic-frequency energy and pressure, to the workpiece in bonding nip 60. The workpiece defined for this illustration represents an article, assembly, or subassembly, many units of which are fabricated as mass-produced items, and can include one or more of web 64, web 66, and the resultant bonded composite 68.

As illustrated in FIG. 6, an absorbent article precursor, commonly referred to as a work piece, can be defined as part of a continuously processed, continuous length, composite web of material . As such work piece is defined, a bond pattern may be formed e.g. at containment flaps 32 preferably before the absorbent article is severed from the web, either as a fully finished or partially finished absorbent article.

While FIG. 6 shows only one method of implementing the bond pattern to form a bonded composite, other processes are contemplated such as creating the bond pattern using a plunge or press ultrasonic horn, rotary ultrasonic horn and anvil, or any other process capable of creating the bond pattern using pressure, thermal energy, ultrasonic energy, adhesive, or the like. Additionally, the materials listed as possible materials capable of comprising an outer cover and a body-side liner, as listed in the description under FIGS. 2–5, are, exemplary only, and not limiting, of the materials contemplated for defining bonded composites of the invention.

A given bond pattern of the invention can employ bond elements employing a variety of configurations. For example, all the bond elements can be arcuate as illustrated in the drawings, but the respective bond elements can employ a variety of sizes, both length, width, and number of radians of arc. Further, not every bond element need comply with the teachings herein so long as the bond pattern performs overall as described, to transfer stresses to the interior of the bond pattern. Typically, such non-conforming bond elements represent a minor fraction of the bond elements employed in the bond pattern, and perform functions other than propagating stresses to the interior of the bond pattern.

With respect to preferred embodiments, the length of a given arcuate bond element, measured along the length of the bond pattern, is preferably about 2 millimeters to about 10 millimeters, more preferably about 6 millimeters to about 7 millimeters. Similarly, width of a given arcuate bond element, measured perpendicular to the length of the bond pattern, is preferably about 2 millimeters to about 10 millimeters, more preferably about 6 millimeters to about 7 millimeters. The width of a given land on, for example, the anvil roll is typically about 0.51 millimeter to about 1.5 millimeters. Height of a given land is typically about 0.51 millimeter to about 1.9 millimeters. The angle traversed by the side wall of a typical such land is about 10 degrees to about 60 degrees, measured against an origin which is perpendicular to the circumference surface of such roll at the locus of the land.

Those skilled in the art will now see that certain modifications can be made to the apparatus and methods herein disclosed with respect to the illustrated embodiments, without departing from the spirit of the instant invention. And while the invention has been described above with respect to the preferred embodiments, it will be understood that the invention is adapted to numerous rearrangements, modifications, and alterations, and all such arrangements, modifications, and alterations are intended to be within the scope of the appended claims.

To the extent the following claims use means plus function language, it is not meant to include there. or in the instant specification, anything not structurally equivalent to what is shown in the embodiments disclosed in the specification.

Having thus described the invention, what is claimed is:

1. A bonded composite, comprising:
   (a) as a first thin-section element, a first layer of thin-section sheet material; and
   (b) a second thin-section element bonded to the first thin-section element by bonds defining a tear-resistant bond pattern,
   the tear-resistant bond pattern having a length represented by first and second ends, and a width represented by first and second side edges of the bond pattern,
   the bond pattern forming an array of separate, and longitudinally spaced, interlocking arcuate bond elements affixing the first and second thin-section elements to each other, each such bond element, away from the first and second ends, operating as a leading bond element with respect to the bond element next disposed toward the second end, and operating as a trailing bond element with respect to the bond element next disposed toward the first end, each such bond element, away from the first and second ends, having corresnonding leading and trailing ends, wherein the bond elements interlock by the trailing end of a leading bond element trailing the a leading end of the respective trailing bond element, each bond element further having spaced first and second end portions corresponding to the leading and trailing ends, and an arcuate intermediate portion between the first and second end portions, at least portions of the arcuate intermediate portions of selected ones of the bond elements being disposed toward the respective first and second side edges of the bond pattern, and all of the ends of the respective bond elements being disposed inwardly of the side edges.

2. A bonded composite as in claim 1, substantial portions of the arcuate intermediate portions of selected ones of the bond elements being disposed toward respective side edges of the bond pattern.

3. A bonded composite as in claim 2 wherein the intermediate portion of a respective said bond element comprises a substantial portion of a single ellipse.

4. A bonded composite as in claim 2 wherein the intermediate portion of a respective said bond element comprises a substantial portion of a circle.

5. A bonded composite as in claim 1 wherein the first end portion of a first said bond element in a given longitudlnaliy-extending line of said bond elements intersects a first imaginary straight line connecting the first and second ends of a second said bond element in the same longitudinally-extending line of said bond elements, and wherein the second end portion of the second said bond element intersects a second imaginary straight line connecting the first and second ends of the first said bond element.

6. A bonded composite as in claim 1 wherein the first end portion of a first said bond element in a given longitudinally-extending line of said bond elements crosses a first imaginary straight line connecting the first and second ends of a second said bond element in the same longitudinally-extending line of said bond elements, and wherein the second end portion of the second said bond element crosses a second imaginary straight line connecting the first and second ends of the first said bond element.

7. A bonded composite as in claim 1 wherein the intermediate portions of respective ones of the bond elements include changes of curvature between concave and convex, and extend from the first side of the bond pattern to the second side of the bond pattern.

8. A bonded composite as in claim 7 wherein the first end portion of a first said bond element in a given longitudinally-extending line of said bond elements intersects a first imaginary straight line connecting the first and second ends of a second said bond element in the same longitudinally-extending line of said bond elements, and wherein the second end portion of the second said bond element intersects a second imaginary straight line connecting the first and second ends of the first said bond element.

9. A bonded composite as in claim 7 wherein the first end portion of a first said bond element in a given longitudinally-extending line of said bond elements crosses a first imaginary straight line connecting the first and second ends of a second said bond element in the same longitudinally-cxtending line of said bond elements, and wherein the second end portion of the second said bond element crosses a second image straight line connecting the first and second ends of the first said bond element.

10. A bonded composite as in claim 1 wherein the bond pattern comprises an array of the bond elements arranged in a longitudinally-repeating and transversely-repeating pattern, such that respective ones of the bond elements are positioned at repeated width locations and at repeated longitudinal spacings along the length of the bond pattern.

11. A bonded composite as in claim 1, the width of the bond pattern between the first and second side edges being about 4 millimeters to about 14 millimeters.

12. A bonded composite as in claim 1, the width of the bond pattern between the first and second side edges being about 5 millimeters to about 12 millimeters.

13. A bonded composite as in claim 1 wherein bonds corresponding to the arcuate bond elements are activated by application of thermal energy alone to at least one of the first and second thin-section elements.

14. A bonded composite as in claim 1 wherein bonds corresponding to the arcuate bond elements are activated by application of ultrasonic-frequency energy to at least one of the first and second thin-section elements.

15. A bonded composite as in claim 1 wherein at least one of the first thin-section element and the second thin-section element comprises a polymeric material selected from the group consisting of polyolefins, polyesters, and polyamides, and copolymers, mixtures, and blends of such polymeric materials.

16. A bonded composite as in claim 1 wherein at least one of the first thin-section element and the second thin-section element comprises a fibrous web defining a multiplicity of randomly-spaced small openings extending from a major surface of the web into the interior of the web.

17. A bonded composite as in claim 1, said bond elements in said bond pattern being arrayed in one or more lines of bond elements, the bond elements in a given one of said lines being longitudinally spaced.

18. A bonded composite as in claim 1, said bond elements in said bond pattern being arrayed in one or more lines of bond elements, the bond elements in a given one of said lines being longitudinally interlocked with each other by a trailing said end of a leading bond element trailing a leading said end of a succeeding one of said bond elements.

19. An absorbent article having a front portion and a rear portion, and a crotch portion between the front portion and the rear portion, the absorbent article comprising:

(a) as a first thin-section element, a first layer of thin-section sheet material;

(b) a second thin-section element bonded to the first thin-section element and correspondingly attached as an element of the absorbent article by bonds defining a tear-resistant bond pattern; and (c) an absorbent core disposed adjacent one of the first thin-section element and the second thin-section element, the tear-resistant bond pattern having a length represented by first and second ends, and a width represented by first and second side edges of the bond pattern, the bond pattern forming an array of separate, and longitudinally spaced, interlocking arcuate bond elements affixing the first and second thin-section elements to each other, each such bond element, away from the first and second ends, operating as a leading bond element with respect to the bond element next disposed toward the second end, and operating as a trailing bond element with respect to the bond element next disposed toward the first ends each such bond element, away from the first and second ends, having corresponding leading and trailing ends, wherein the bond elements interlock by the trailing end of a leading bond element trailing the leading end of the respective trailing bond element, said bond elements having spaced first and second end portions corresponding to the leading and trailing ends, and arcuate intermediate portions between the first and second end portions, at least portions of the arcuate intermediate portions of selected ones of the bond elements being disposed toward the respective first and second side edges of the bond pattern, all of the ends of the respective bond elements being disposed inwardly of the side edges.

20. An absorbent article as in claim 19 wherein the first thin-section element comprises an outer cover and wlerein the outer cover comprises a polymeric film having a composition comprising primarily polyethylene or polypropylene, or a mixture or copolymer comprising polyethylene and polypropylene.

21. An absorbent article as in claim 19 wherein the second thin-section element comprises a body side liner and wherein the body side liner comprises a material selected from the group consisting of porous foams, reticulated foams, apertured polymeric films, polymeric fibers, and natural fibers.

22. An absorbent article as in claim 19 wherein the body side liner comprises a mixture of materials selected from the group consisting of porous foams, reticulated foams, apertured polymeric films, polymeric fibers, and natural fibers.

23. An absorbent article as in claim 19 wherein the absorbent core comprises a mati of hydrophilic fibers.

24. An absorbent article as in claim 19 wherein the intermediate portion of a respective said bond element comprises a substantial portion of a single ellipse.

25. An absorbent article as in claim 19 wherein the intermediate portion of a respective said bond element comprises a substantial portion of a circle.

26. An absorbent article as in claim 19 wherein the first end portion of a first said bond element in a given longitudinally-extending line of said bond elements intersects a first imaginary straight line connecting the first and second ends of a second said bond element in the same longitudinally-extending fine of said bond elements, and wherein the second end portion of the second said bond element intersects a second imaginary straight line connecting the first and second ends of the first said bond element.

27. An absorbent article as in claim 19 wherein the first end portion of a first said bond element in a given longitudinally-extending line of said bond elements crosses a first imaginary straight line connecting the first and second ends of a second said bond element in the same longitudinally-extending line of said bond elements, and wherein the second end portion of the second said bond element crosses a second imaginary straight line connecting the first and second ends of the first said bond element.

28. An absorbent article as in claim 19 wherein the bond pattern comprises an array of the bond elements arranged in a longitudinally-repeating and transversely-repeating pattern, such that respective ones of the bond elements are positioned at repeated width locations and at repeated longitudinal spacings along the length of the bond pattern.

29. An absorbent article as in claim 19, the length of the bond pattern extending firom the front portion of the absorbent article to the rear portion of the absorbent article.

30. An absorbent article as in claim 19 wherein the crotch portion of the absorbent article is devoid of the bond pattern.

31. An absorbent article as in claim 19, substantial portions of the arcuate intermediate portions of selected ones of the bond elements being disposed toward respective side edges of the bond pattern.

32. An absorbent article as in claim 19 wherein the first thin-section element comprises an outer cover, wherein the second thin-section element comprises a body side liner, and wherein at least one of the outer cover and the body side liner comprises a polymeric material selected from the group consisting of polyolefins, polyesters, and polyamides, and mixtures, copolymers, and blends of such polymeric materials.

33. An absorbent article as in claim 19, said bond elements in said bond pattern being arrayed in one or more lines of bond elements, the bond elements in a given one of said lines being longitudinally spaced.

34. An absorbent article as in claim 19, said bond elements in said bond pattern being arrayed in one or more lines of bond elements, the bond elements in a given one of said lines being longitudinally interlocked with each other by a trailing said end of a leading bond element trailing a leading said end of a succeeding one of said bond elements.

35. An absorbent article as in claim 19 wherein the absorbent article comprises a feminine hygiene article.

36. An absorbent article as in claim 19 wherein the absorbent article comprises a diaper.

37. An absorbent article as in claim 19 whee the absorbent article comprises an adult incontinence product.

38. An absorbent article as in claim 19, the width of the bond pattern between the first and second side edges being about 4 millimeters to about 14 millineters.

39. An absorbent article as in claim 19, the width of the bond pattern between the fist and second side edges being about 5 millimeters to about 12 millimeters.

40. An absorbent article as in claim 19 wherein bonds corresponding to the arcuate bond elements are activated by application of thermal energy alone to at least one of the first and second thin-section elements.

41. An absorbent article as in claim 19 wherein bonds corresponding to the arcuate bond elements are activated by application of ultrasonic-frequency energy to at least one of the first and second thin-section elements.

42. An absorbent article having a front portion and a rear portion, and a crotch portion between the front portion and the rear portion, the absorbent article comprising:

(a) as a first thin-section element, a first layer of thin-section sheet material;

(b) a second thin-section element bonded to the first thin-section element and correspondingly attached as an element of the absorbent article by bonds defining a tear-resistant bond pattern; and (c) an absorbent core disposed adjacent one of the first thin-section element and the second thin-section element, the tear-resistant bond pattern having a length represented by first and second ends, and a width represented by first and second side edges of the bond pattern, the bond pattern forming an array of separate, and spaced, longitudinally interlocking arcuate bond elements affixing the first and second thin-section elements to each other, each such bond element, awav from the first and second ends, operating as a leading bond element with respect to the bond element next disposed toward the second end, and operating as a trailing bond element with respect to the bond element next disposed toward the first end, each such bond element, away from the first and second ends having corresponding leading and trailing ends, wherein the bond elements interlock by the trailing end of a leading bond element trailing the leading end of the respective trailing bond element, said bond elements having spaced first and second end portions corresponding to the leading and trailing ends, and arcuate intermediate portions between the first and second end portions, at least portions of the arcuate intermediate portions of selected ones of the bond elements being disposed toward the respective first and second side edges of the bond pattern, all of the ends of the respective bond elements being disposed inwardly of the side edges, and wherein the intermediate portions of respective ones of the bond elements include change of curvature between concave and convex.

43. An absorbent article as in claim 42 wherein the intermediate portions of the bond elements extend from the first side of the bond pattern to the second side of the bond pattern.

44. An absorbent article as in claim 43 wherein the first end portion of a first said bond element in a given longitudinally-extending line of said bond elements intersects a first imaginary straight line connecting the first and second ends of a second said bond element in the same longitudinally-extending line of said bond elements, and wherein the second end portion of the second said bond element intersects a second imaginary straight line connecting the first and second ends of the first said bond element.

45. An absorbent article as in claim 43 wherein the first end portion of a first said bond element in a given longitudinally-extending line of said bond elements crosses a first imaginary straight line connecting the first and second ends of a second said bond element in the same longitudinally-extending line of said bond elements, and wherein the second end portion of the second said bond element crosses a second imaginary straight line connecting the first and second ends of the first said bond element.

46. An absorbent article as in claim 43 wherein the bond pattern comprises an array of the bond elements arranged in a longitudinally-repeating and transversely-repeating pattern, such that respective ones of the bond elements are positioned at repeated width locations and at repeated longitudinal spacings along the length of the bond pattern.

47. An absorbent article as in claim 46, the length of the bond pattern extending from the front portion to the rear portion of the absorbent article.

48. An absorbent article as in claim 46 wherein the crotch portion of the absorbent article is devoid of the bond pattern.

49. An absorbent article as in claim 42, said bond elements in said bond pattern being arrayed in one or more lines of bond elements, the bond elements in a given one of said lines being longitudinally spaced.

50. An absorbent article as in claim 42, said bond elements in said bond pattern being arrayed in one or more lines of bond elements, the bond elements in a given one of said lines being longitudinally interlocked with each other by a trailing said end of a leading bond element trailing a leading said end of a succeeding one of said bond elements.

51. A bonded composite, comprising:

(a) as a first thin-section element, a first layer of thin-section sheet material; and (b) a second thin-section element bonded to the first thin-section element by bonds defining a tear-resistant bond pattern, the tear-resistant bond pattern having a length represented bv first and second ends, and a width represented by first and second side edges of the bond pattern, the bond pattern forming an array of separate, and spaced, longitudinally interlocking arcuate bond elements affixing the first and second thin-section elements to each other, each such bond element, tawag from the first and second ends, operating as a leading bond element with respect to the bond element next disposed toward the second end, and operating as a trailing bond element with respect to the bond element next disposed toward the first end each such bond element, away from the first and second ends, having corresponding leading and trailing ends, wherein the bond elements interlock by the trailing end of a leading bond element trailing the leading end of the respective trailing bond element, each bond element further having spaced first and second end portions corresponding to the leading and trailing ends, and an arcuate intermediate portion between the first and second end portions, at least portions of the arcuate intermediate portions of selected ones of the bond elements being disposed toward the respective first and second side edges of the bond pattern, and all of the ends of the respective bond elements being disposed inwardly of the side edges.

52. A bonded composite as in claim 51, substantial portions of the arcuate intermediate portions of selected ones of the bond elements being disposed toward respective side edges of the bond pattern.

53. A bonded composite as in claim 51 wherein the first end portion of a first said bond element in a given longitudinally-extending line of said bond elements intersects a first imaga straight line connecting the first and second ends of a second said bond element in the same longitudinally-extending line of said bond elements, and wherein the second end portion of the second said bond element intersects a second imaginary straight line connecting the first and second ends of the first said bond element.

54. A bonded composite as in claim 51 wherein the first end portion of a first said bond element in a given longitudinally-extending line of said bond elements crosses a first imaginary straight line connecting the first and second ends of a second said bond element in the same longitudinally-extending line of said bond elements, and wherein the second end portion of the second said bond element crosses a second imagry straight line connecting the first and second ends of the first said bond element.

55. A bonded composite as in claim 51 wherein the intermediate portions of respective ones of the bond elements include changes of curvature between concave and convex, and extend from the first side of the bond pattern to the second side of the bond pattern.

56. A bonded composite as in claim 51, said bond elements in said bond pattern being arrayed in one or more lines of bond elements, the bond elements in a given one of said lines being longitudinally spaced.

57. A bonded composite as in claim 51, said bond elements in said bond pattern being arrayed in one or more lines of bond elements, the bond elements in a given one of said lines being longitudinally interlocked with each other by a trailing said end of a leading bond element trailing a leading said end of a succeeding one of said bond elements.

58. An absorbent artile having a front portion and a rear portion, and a crotch portion between the front portion and the rear portion, the absorbent article comprising:
(a) as a first thin-section element, a first layer of thin-section sheet material;
(b) a second thin-section element bonded to the first thin-section element and correspondingly attached as an element of the absorbent article by bonds defining a tear-resistant bond pattern; and
(c) an absorbent core disposed adjacent one of the first thin-section element and the second thin-section element,
the tear-resistant bond pattern having a length represented by first and second ends and a width represented by first and second side edges of the bond pattern,
the bond pattern forming an array of separate, and spaced, longitudinally interlocking arcuate bond elements affixing the first and second thin-section elements to each other, eagh such bond element, away from the first and second ends, operating as a leading bond element with respect to the bond element next disposed toward the second end, and operating as a trailing bond element with respect to the bond element next disposed toward the first end, each such bond element away from the first and second ends, having corresponding leading and trailing ends, wherein the bond elements interlock by the trailing end of a leading bond element trailing the leading end of the respective trailing bond element, said bond elements having spaced first and second end portions corresponding to the leading and trailing ends, and arcuate intermediate portions between the first and second end portions, at least portions of the arcuate intermediate portions of selected ones of the bond elements being disposed toward the respective first and second side edges of the bond pattern, all of the ends of the respective bond elements being disposed inwardly of the side edges.

59. An absorbent article as in claim 58, substantial portions of the arcuate intermediate portions of selected ones of the bond elements being disposed toward respective side edges of the bond pattern.

60. An absorbent article as in claim 58 wherein the first end portion of a first said bond element in a given longitudinally-extending line of said bond elements intersects a first imaginary straight line connecting the first and second ends of a second said bond element in the same longitudinally-extending line of said bond elements, and wherein the second end portion of the second said bond element intersects a second imaginary straight line connecting the first and second ends of the first said bond element.

61. An absorbent article as in claim 58 wherein the first end portion of a first said bond element in a given longitudinally-extending line of said bond elements crosses a first imaginary straight line connecting the first and second ends of a second said bond element in the same longitudinaily-extending line of said bond elements, and wherein the second end portion of the second said bond element crosses a second imaginary straight line connecting the first and second ends of the fist said bond element.

62. An absorbent article as in claim 58 wherein the intermediate portions of respective ones of the bond elements include changes of curvature between concave and convex, and extend from the first side of the bond pattern to the second side of the bond pattern.

63. An absorbent article as in claim 58, said bond elements in said bond pattern being arrayed in one or more lines of bond elements, the bond elements in a given one of said lines being longitudinally spaced.

64. An absorbent article as in claim 58, said bond elements in said bond pattern being arrayed in one or more lines of bond elements, the bond elements in a given one of said lines being longitudinally interlocked with each other by a trailing said end of a leading bond element trailing a leading said end of a succeeding one of said bond elements.

65. A bonded composite, comprising:
(a) as a first thin-section element, a first layer of thin-section sheet material; and
(b) a second thin-section element bonded to the first thin-section element by bonds defining a tear-resistant bond pattern,
the tear-resistant bond pattern having a length represented by first and second ends, and a width represented by first and second side edges of the bond pattern,
the bond pattern forming an array comprising longitudinally-extending first and second lines of bond elements affixing the first and second thin-section elements to each other, each line of bond elements of the first line of bond elements interlocking with respective ones of the bond elements of the second line of bond elements, each bond element in the first and second lines of bond elements having spaced first and second ends and corresponding end portions, and an intermediate portion, sequential said bond elements in a given line of said bond elements comprising curved portions of the respective lines at the intermediate portions of the respective bond elements, wherein convex sides of said curved portions are disposed toward opposing ones of the respective first and second side edges.

66. A bonded composite as in claim 65 wherein the ends of said bond elements are disposed substantially inwardly of the side edges of said bond pattern.

67. A bonded composite as in claim 65, substantial portions of the arcuate intermediate portions of selected ones of the bond elements being disposed toward respective side edges of the bond pattern.

68. A bonded composite as in claim 65 wherein the first end portion of a first said bond element in a given longitudinauy-extending line of said bond elements intersects a first imaginary straight line connecting the first and second ends of a second said bond element in the same longitudinally-extending line of said bond elements, and wherein the second end portion of the second said bond element intersects a second imaginary straight line connecting the first and second ends of the first said bond element.

69. A bonded composite as in claim 65 wherein the first end portion of a first said bond element in a given longitudinally-extending line of said bond elements crosses a first imagiary straight line connecting the first and second ends of a second said bond element in the same longitudinally-extending line of said bond elements, and wherein the second end portion of the second said bond element crosses a second imaginary straight line connecting the first and second ends of the first said bond element.

70. A bonded composite as in claim 65 wherein the intermediate portions of respective ones of the bond elements include changes of curvature between concave and convex, and extend from the first side of the bond pattern to the second side of the bond pattern.

71. A bonded composite as in claim 65, said bond elements in said bond pattern being arrayed in one or more lines of bond elements, the bond elements in a given one of said lines being longitudinally spaced 72. A bonded composite as in claim 65, said bond elements in said bond pattern being arrayed in one or more lines of bond elements, the bond elements in a given one of said lines being longitudinally interlocked with each other by a trailing said end of a leading bond element trailing a leading said end of a succeeding one of said bond elements.

73. An absorbent article, comprising:

(a) as a first thin-section element, a first layer of thin-section sheet material;

(b) a second thin-section element bonded to the first thin-section element and correspondingly attached as an element of the absorbent article by bonds defining a tear-resistant bond pattern; and (c) an absorbent core disposed adjacent one of the first thin-section element and the second thin-section element, the tear-resistant bond pattern having a length, and a width represented by first and second side edges of the bond pattern, the bond pattern forming an array comprising longitudinally-extending first and second lines of bond elements affixing the first and second thin-section elements to each other, bond elements of the first line of bond elements interlocking ones of the bond elements of the second line of bond elements, each bond element in the first and second lines of bond elements having spaced first and second ends and corresponding end portions, and an intermediate portion, sequential said bond elements in a given line of said bond elements comprising curved portions of the respective lines at the intermediate portions of the respective bond elements, wherein convex sides of said curved portions are disposed toward opposing ones of the respective first and second side edges.

74. An absorbent article as in claim 73 wherein the ends of said bond elements are disposed substantially inwardly of the side edges of said bond pattern.

75. An absorbent article as in claim 73, substantial portions of the arcuate intermediate portions of selected ones of the bond elements being disposed toward respective side edges of the bond pattern.

76. An absorbent article as in claim 73 wherein the first end portion of a first said bond element in a given longitudinally-extending line of said bond elements intersects a first imaginary straight line connecting the first and second ends of a second said bond element in the same longitudinally-extending line of said bond elements, and wherein the second end portion of the second said bond element intersects a second imaginary straight line connecting the first and second ends of the first said bond element.

77. An absorbent article as in claim 73 wherein the first end portion of a first said bond element in a given longitudinally-extendinp line of said bond elements crosses a first imaginary straight line connecting the first and second ends of a second said bond element in the same longitudinally-extending line of said bond elements, and wherein the second end portion of the second said bond element crosses a second imaginary straight line connecting the first and second ends of the first said bond element.

78. An absorbent article as in claim 73 wherein the intermediate portions of respective ones of the bond elements include changes of curvature between concave and convex, and extend from the first side of the bond pattern to the second side of the bond pattern.

79. An absorbent article as in claim 73, said bond elements in said bond pattern being arrayed in one or more lines of bond elements, the bond elements in a given one of said lines being longitudinally spaced.

* * * * *